United States Patent [19]

Hibie et al.

[11] Patent Number: 5,243,085

[45] Date of Patent: Sep. 7, 1993

[54] STARTING MATERIALS FOR IMPROVED RADIATION HARDENABLE DILUENTS

[75] Inventors: Francis A. Hibie, Bound Brook, N.J.; Robert A. LieBerman, Naperville, Ill.; Ira M. Rose, Milburn, N.J.

[73] Assignee: Diamond Shamrock Chemical Co., Dallas, Tex.

[21] Appl. No.: 925,535

[22] Filed: Aug. 5, 1992

Related U.S. Application Data

[60] Division of Ser. No. 696,471, May 6, 1991, Pat. No. 5,159,119, which is a division of Ser. No. 472,138, Jan. 30, 1990, Pat. No. 5,053,554, which is a continuation of Ser. No. 74,991, Jul. 17, 1987, abandoned, which is a division of Ser. No. 849,301, Apr. 8, 1986, Pat. No. 4,876,384, which is a continuation-in-part of Ser. No. 725,801, Apr. 22, 1985, abandoned, and a continuation-in-part of Ser. No. 797,483, Nov. 13, 1985, abandoned.

[51] Int. Cl.$^5$ .......................................... C07C 43/257
[52] U.S. Cl. .................................................. 568/609
[58] Field of Search ........................................ 568/609

[56] References Cited

FOREIGN PATENT DOCUMENTS 47-20074  9/1972  Japan ................................. 568/609

*Primary Examiner*—Howard T. Mars
*Attorney, Agent, or Firm*—Ernest G. Szoke; Wayne C. Jaeschke; Norvell E. Wisdom, Jr.

[57] ABSTRACT

Radiation curable compositions containing outstanding reactive diluents have been developed. The diluents are lower alkyl ether acrylates and methacrylates of particular alkoxylated and non-alkoxylated polyols.

Examples are mono-methoxy trimethylolpropane diacrylate, mono-methoxy neopentyl glycol monoacrylate and mono-methoxy, ethoxylated neopentyl glycol monoacrylate having an average of about two moles of ethylene oxide.

1 Claim, No Drawings

STARTING MATERIALS FOR IMPROVED RADIATION HARDENABLE DILUENTS

RELATED APPLICATION

This application is a division of copending application Ser. No. 696,471 filed May 6, 1991 and now U.S. Pat. No. 159,119, which was a division of application Ser. No, 472,138 filed Jan. 30, 1990 and now U.S. Pat. 5,053,554, which was a continuation of application Ser. No. 74,991 filed Jul. 17, 1987 and now abandoned, which was a division of application Ser. No. 849,301 filed Apr. 8, 1986, now U.S. Pat. No. 4,876,384, which was a continuation-in-part of application Ser. No. 725,801, filed Apr. 22, 1985 now abandoned and a continuation-in-part of application Ser. No. 797,483, filed Nov. 13, 1985 now abandoned.

BACKGROUND OF THE INVENTION

1. Field of the Invention

This invention relates to radiation curable diluents which are lower alkyl ether (alkoxy) acrylates and methacrylates of particular alkoxylated and non-alkoxylated polyols and to radiation curable compositions containing same.

2. Description of the Prior Art

Radiation curable or hardenable compositions, particularly for coating applications, are known in the art. In view of the restrictions on solvent content in the atmosphere, increasing efforts have been made to provide completely polymerizable systems which do not contain any volatile components, but instead consist of constituents which form either the whole or a part of the hardened film itself.

Although radiation curable oligomers and polymers form the backbone of a radiation curable coating, they cannot normally be used alone because of their high viscosity and poor application properties. Viscosity reduction is usually accomplished by use of reactive monomers. These not only act as diluents for the system, but also copolymerize with the oligomers and polymers and contribute to the final properties of the cured film. Examples of reactive monomers, also referred to as radiation curable diluents, are multifunctional acrylates and methacrylates of alkoxylated and non-alkoxylated polyols. Reference is made to the following U.S. Pat. Nos. for examples of same.

3,594,410—Cohen et al, Jul. 20, 1971
3,857,822—Frass, Dec. 31, 1974
4,058,443—Murata et al, Nov. 15, 1977
4,088,498—Faust, May 9, 1978
4,177,074—Proskow, Dec. 4, 1979
4,179,478—Rosenkranz et al, Dec. 18, 1979
4,180,474—Schuster et al, Dec. 25, 1979
4,382,135—Sinka et al, May 3, 1983

Conventional multifunctional acrylates and methacrylates such as trimethylolpropane triacrylate, trimethylolpropane trimethacrylate, pentaerythritol triacrylate and 1,6-hexanediol diacrylate and dimethacrylate were the major reactive monomers developed and introduced in the 1970's for use in radiation curable coatings. Although they exhibited several of the desired characteristics of an ideal monomer, there were many problems and limitations associated with their use.

Trifunctional types, e.g., trimethylolpropane triacrylate and pentaerythritol triacrylate, were fast curing but produced brittle films with severe shrinkage and poor adhesion to a variety of substrates. Moreover, their higher intrinsic viscosities contributed to poorer solvency and inadequate viscosity reduction characteristics which limited their use in many applications. Difunctional types, e.g., 1,6-hexanediol diacrylate and dimethacrylate exhibited superior viscosity reduction but poor or slower cure response. Many of these monomers also posed serious skin irritancy problems in compounding and processing of the coatings.

Thus, a need was shown for reactive monomers with fast cure response (high reactivity), low intrinsic viscosity, low shrinkage and excellent solvating or viscosity reducing properties.

SUMMARY OF THE INVENTION

Outstanding reactive monomers, i.e., radiation hardenable diluents, have been developed for use in radiation curable or hardenable compositions containing radiation curable or hardenable oligomers. These radiation curable diluents are characterized by improved cure response, low intrinsic viscosity, low shrinkage (as a film) and excellent solvating or viscosity reducing properties. These last two attributes permit use of higher quantities of oligomer in the formulation to improve final properties of the cured coating. This is because the oligomers are the major components of radiation hardenable coatings and are responsible for the majority of the physical characteristics of the cured film. Such combination of properties has not heretofore been achieved. Indeed, such improved combination of properties more closely approaches the attributes of an ideal radiation curable monomer. These reactive monomers are one or a mixture of compositions having formulas I through IV.

   I where:

$C_5$ or $C_6$

R′ = at least one of $C_1$ to $C_6$
R″ = H—, $CH_3$—, $CH_3CH_2$— or mixtures
R‴ = H—, $CH_3$— or mixtures
a = 1, 2 or 3
m = 0 to about 6
n = 0 to about 6 with the proviso m+n does not exceed about 6, and with the proviso when $C_5$ is linear, m+n is about 1 to about 6

II mono-lower alkoxy trans-1,4-cyclohexane dimethylol monoacrylate and mono-lower alkoxy trans-1,4-cyclohexane dimethylol monomethacrylate

III mono-lower alkoxy 2,2,4-trimethyl-1,3-pentanediol monoacrylate and mono-lower alkoxy 2,2,4-trimethyl-1,3-pentanediol monomethacrylate

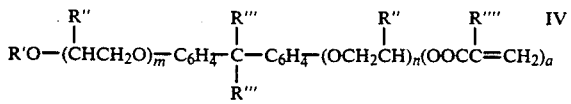

where:
- R' = at least one of $C_1$ to $C_6$
- R" = H—, $CH_3$—, $CH_3CH_2$— or mixtures
- R'" = H— or $CH_3$—
- R"" = H—, $CH_3$— or mixtures
- a = 1
- m = 0 to about 6
- n = 0 to about 6
- m+n = 0 to about 6

In the above formulas, R is straight or branched and for example can be derived from glycerol, neopentyl glycol, 1,6-hexanediol, trimethylolethane, trimethylolpropane and pentaerythritol, R' is straight or branched and for example can be methyl, ethyl, propyl, isopropyl, butyl, isobutyl, amyl or n-hexyl and lower alkoxy can be methoxy, ethoxy, propoxy, isopropoxy, butoxy, pentoxy or hexyloxy.

Examples of reactive monomers falling within the foregoing formulas are:

mono-methoxy trimethylolpropane diacrylate
mono-methoxy, ethoxylated trimethylol propane diacrylate having an average of three moles of ethylene oxide
mono-methoxy, propoxylated trimethylol propane diacrylate having an average of three moles of propylene oxide
mono-methoxy 1,6-hexanediol monoacrylate
mono-methoxy pentaerythritol triacrylate
mono-methoxy, propoxylated pentaerythritol triacrylate having an average of four moles of propylene oxide
mono-methoxy neopentyl glycol monoacrylate
mono-methoxy, ethoxylated neopentyl glycol monoacrylate having an average of two moles of ethylene oxide
mono-methoxy, propoxylated neopentyl glycol monoacrylate having an average of two moles of propylene oxide
mono-methoxy trans-1,4-cyclohexane dimethylol monoacrylate
mono-methoxy propoxylated glycerol diacrylate having an average of three moles of propylene oxide
mono-methoxy propoxylated hexane glycol monoacrylate having an average of two moles of propylene oxide
mono-methoxy 2,2,4-trimethyl 1,3-pentane diol monoacrylate
mono-methoxy ethoxylated 2,2-bis(p-hydroxyphenyl)-propane monoacrylate having an average of four moles of ethylene oxide
mono-methoxy bis(p-hydroxyphenyl)methane monoacrylate
mono-methoxy trimethylolpropane dimethacrylate
mono-methoxy, ethoxylated trimethylol propane dimethacrylate having an average of three moles of ethylene oxide
mono-methoxy, propoxylated trimethylol propane dimethacrylate having an average of three moles of propylene oxide
mono-methoxy 1,6-hexanediol monomethacrylate
mono-methoxy pentaerythritol trimethacrylate
mono-methoxy, propoxylated pentaerythritol trimethacrylate having an average of four moles of propylene oxide
mono-methoxy neopentyl glycol monomethacrylate
mono-methoxy, ethoxylated neopentyl glycol monomethacrylate having an average of two moles of ethylene oxide
mono-methoxy, propoxylated neopentyl glycol monomethacrylate having an average of two moles of propylene oxide
mono-methoxy trans-1,4-cyclohexane dimethylol monomethacrylate
mono-methoxy propoxylated glycerol dimethacrylate having an average of three moles of propylene oxide
mono-methoxy propoxylated hexane glycol monomethacrylate having an average of two moles of propylene oxide
mono-methoxy 2,2,4-trimethyl 1,3-pentane diol monomethacrylate
mono-methoxy ethoxylated 2,2-bis(p-hydroxyphenyl)-propane monomethacrylate having an average of four moles of ethylene oxide
mono-methoxy bis(p-hydroxyphenyl)methane monomethacrylate As stated above, improved radiation hardenable compositions have been developed which contain at least one radiation hardenable oligomer and at least one of the novel reactive monomers set forth in formulas I, II, III and IV. In addition, it has been discovered that lower alkyl ether acrylates and methacrylates having the structure of formula V below function as effective reactive diluents and that improved radiation hardenable compositions can be prepared using at least one radiation hardenable oligomer and at least one lower alkyl ether acrylate or methacrylate having the structure of formula V.

where:

or $-CH_2-CH_2-CH_2-CH_2-$
- R' = at least one of $C_1$ to $C_6$
- R" = H—, $CH_3$—, $CH_3CH_2$— or mixtures
- R'" = H—, $CH_3$— or mixtures
- a = 1
- m = 0 to about 6
- n = 0 to about 6
- m+n = 0 to 6

In the above formula, R is derived from ethylene glycol, propylene glycol and butylene glycol while R' is straight or branched and for example can be methyl, ethyl, propyl, isopropyl, butyl, isobutyl, amyl or n-hexyl.

Examples of additional reactive monomers falling within formula V are:
mono-propoxy ethylene glycol monoacrylate
mono-n-butoxy ethylene glycol monoacrylate
mono-methoxy diethylene glycol monoacrylate
mono-ethoxy diethylene glycol monoacrylate
mono-n-butoxy diethylene glycol monoacrylate
mono-methoxy triethylene glycol monoacrylate mono-methoxy propylene glycol monoacrylate
mono-methoxy tripropylene glycol monoacrylate
mono-propoxy ethylene glycol monomethacrylate
mono-n-butoxy ethylene glycol monomethacrylate
mono-methoxy diethylene glycol monomethacrylate
mono-ethoxy diethylene glycol monomethacrylate
mono-n-butoxy diethylene glycol monomethacrylate
mono-methoxy triethylene glycol monomethacrylate
mono-methoxy propylene glycol monomethacrylate
mono-methoxy tripropylene glycol monomethacrylate Radiation curable or hardenable compositions which contain the radiation curable or hardenable monomers of formulas I, II, III, IV and V are characterized by the enhanced properties shown by the neat monomers when compared with conventional acrylates.

Stated another way, the improved radiation hardenable compositions contain at least one radiation hardenable oligomer and at least one reactive monomer set forth in formula V A as well as in the aforementioned formulas II, III and IV.

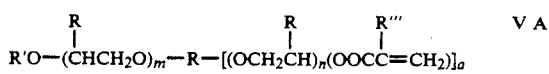

where:
R = $C_2$ to $C_6$
R' = at least one of $C_1$ to $C_6$
R'' = H—, $CH_3$—, $CH_3CH_2$— or mixtures
R''' = H—, $CH_3$ or mixtures
a = 1, 2 or 3
m = 0 to about 6
n = 0 to about 6 and with the proviso m + n does not exceed about 6

In the above formula, R is straight or branched and for example can be derived from ethylene glycol, propylene glycol, butylene glycol, glycerol, neopentyl glycol, 1,6-hexane diol, trimethylolethane, trimethylolpropane and pentaerythritol while R' is straight or branched and for example can be methyl, ethyl, propyl, isopropyl, butyl, isobutyl, amyl or n-hexyl.

Further, the reactive monomers falling within formulas I, II, III, IV, V and V A have no free hydroxyl groups.

In the list of reactive monomers falling within the foregoing formulas I, II, III, IV, V and V A, those which are mono-ethers of alkoxylated polyols have been prepared by forming the mono-ether of the alkoxylated polyol.

In addition, certain of the reactive monomers of formulas I, II, III and IV are prepared from novel

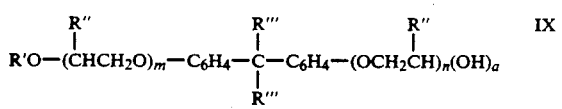

where:
R' = at least one of $C_1$ to $C_6$
R'' = H—, $CH_3$—, $CH_3CH_2$— or mixtures
R''' = H— or $CH_3$—
a = 1
m = 0 to about 6
n = 0 to about 6 with the proviso m + n = 0 to about 6

In the above formulas, R is straight or branched and for example can be derived from neopentyl glycol, 1,6-hexanediol, glycerol, trimethylolethane, trimethylolpropane and pentaerythritol, R' can be methyl, ethyl, propyl, isopropyl, butyl, isobutyl, amyl or n-hexyl and lower alkoxy can be methoxy, ethoxy, propoxy, isopropoxy, butoxy, pentoxy or hexyloxy.

Examples of these monoethers are:
mono-methyl ether of propoxylated pentaerythritol having an average of about four moles of propylene oxide
mono-methyl ether of ethoxylated trimethylolpropane having an average of three moles of ethylene oxide
mono-methyl ether of propoxylated trimethylolpropane having an average of three moles of propylene oxide
mono-methyl ether of 1,6-hexanediol
mono-methyl ether of neopentyl glycol
mono-methyl ether of ethoxylated neopentyl glycol having an average of about two moles of ethylene oxide
mono-methyl ether of propoxylated neopentyl glycol having an average of two moles of propylene oxide
mono-ethers of particular polyols, such ethers having the structure of formulas VI, VII, VIII and IX.

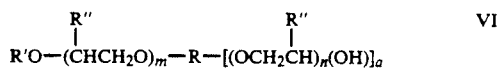

where:

$C_5$ or $C_6$
R' = at least one of $C_1$ to $C_6$
R'' = H—, $CH_3$—, $CH_3CH_2$— or mixtures
a = 1, 2 or 3
m = 0 to about 6
n = 0 to about 6 and when m + n = 0, a = 1 with the proviso m + n does not exceed about 6 and with the proviso when $C_5$ is linear, m + n is about 1 to about 6

VII mono-lower alkoxy trans-1,4-cyclohexane dimethylol (also known as mono-lower alkoxy trans-1,4-cyclohexanedimethanol)

VIII mono-lower alkoxy 2,2,4-trimethyl-1,3-pentanediol
mono-methyl ether of propoxylated glycerol having an average of three moles of propylene oxide
mono-methyl ether of trans-1,4-cyclohexanedimethanol
mono-methyl ether of 2,2-bis(p-hydroxyphenyl)propane having an average of four moles of ethylene oxide
mono-methyl ether of bis(p-hydroxyphenyl)methane
mono-methyl ether of 2,2,4-trimethyl-1,3 pentane diol The diluents can be prepared as follows as shown below:

A. Preparation of mono-lower alkyl ethers of non-alkoxylated polyols (ether bases)

The desired polyol is charged to a pressure reactor equipped with a sparge tube, thermometer, stirrer and sample port. The reactor can be heated or cooled automatically as required. The polyol is then heated to temperatures up to 150° C. under nitrogen, preferably 60°-70° C. Slight nitrogen pressure is applied and a lower alkyl chloride such as methyl chloride, ethyl chloride, propyl chloride or n-butyl chloride is added slowly at molar ratios to form the mono-ether of the polyol (ether base).

The reaction may be catalyzed by the use of a basic catalyst such as caustic soda in flake or prill form or hydrated lime which is introduced in two portions. After the ether base is formed, the product is washed, stripped, dried and filtered using standard procedures.

B. Preparation of mono-lower alkyl ethers of alkoxylated polyols (ether base)

A pressure reactor is charged with alkoxylated polyol and about one-half of the formula weight of sodium hydroxide and pressured with nitrogen. Full vacuum is applied for about one-half hour and reactor repressured with nitrogen. Then one-half of the formula weight of a lower alkyl chloride such as disclosed above is added. Reaction is allowed to continue until pressure remains constant. Evacuation with nitrogen is carried out and the reactor is charged with the remainder of the sodium hydroxide. The reactor is evacuated, pressured with nitrogen and the remainder of the lower alkyl chloride introduced slowly. After addition, reaction continues until pressure remains constant. Then, the resulting product is washed, stripped to dryness and filtered using standard procedures.

C. Preparation of the acrylates and methacrylates of A and B

The above ether bases and acrylic or methacrylic acid are added to a reactor equipped with a stirrer, thermometer, sparge tube and azeotropic collecting equipment. The reaction is carried out in the presence of a low boiling point reflux solvent such as benzene, toluene or other aromatic and aliphatic solvents at temperatures ranging from 50°-150° C., preferably from 90°-100° C. Direct esterification is carried out with an excess of acrylic acid or slight excess of methacrylic acid being present. Water of reaction is collected as the reaction progresses. An esterification catalyst may be employed in the esterification reaction. Examples include p-toluene sulfonic acid, methane sulfonic acid and generally any of the sulfonic or carboxylic acids or an ion exchange esterification catalyst such as divinyl benzene-styrene sulfonic acid reaction products.

Acrylation and methacrylation may also be carried out by transesterification or by utilizing a Schotten-Baumann procedure using acryloyl chloride. Procedures, inhibitors and catalysts for these alternate procedures are well known in the art and need not be repeated here.

When carrying out the esterification, transesterification or acid chloride acrylations, methacrylations, a polymerization inhibitor may be utilized. Examples of such materials include quinones, such as hydroquinone, toluhydroquinone, hydroquinone monomethyl ether (p-methoxyphenol), the various phenols, p-tert-butylcatechol, 2,4-dichloro-6-nitrophenol, n-propyl gallate, di-tertbutyl-p-cresol, 2,2'-methylenebis(4-methyl-6-tert-butylphenol), 1-amino-7-naphthol, p-benzoquinone, 2,6-dichloro-p-benzoquinone, 2-amino-1,4-naphthoquinone, 3-aminoanthraquinone, diphenylamine, p-nitrosodimethylaniline, alpha and beta-naphthylamine, nitrobenzene, phenothiazine, N-nitrosodimethylamine, hexamethylphosphoramide, n-dodecyl mercaptan, benzenethiol, 2,2-diphenyl-1-picryl-hydrazyl(phenyl hydrazine), divinylacetylene and various antimony and copper salts. Most preferred among the inhibitors are paramethoxyphenol, hydroquinone, phenothiazine, and nitrobenzene. The inhibitors should be added to the reaction mixture in the range of about 50–1000 parts per million (ppm), preferably about 100–400 ppm per 100 parts of final product (ester).

Following esterification, transesterification, etc., the products may be purified by standard purification methods, including solvent extraction, washing, drying, evaporation and distillation.

It must be appreciated that when preparing alkoxylated polyol, the addition of alkylene oxide to polyol is random and the total number of moles of added alkylene oxide may be distributed equally or unequally among the hydroxyl groups of the polyol and the foregoing structures are intended to encompass such structures. Further, when a mono-lower alkyl ether is prepared from an alkoxylated polyol, the alkyl group is very likely attached to an alkoxylated hydroxyl group of the alkoxylated polyol and the foregoing structures are intended to encompass compounds prepared in this manner.

Although less preferred, if desired in the case of mono-lower alkyl ether acrylates and methacrylates of alkoxylated polyols, the mono-ether of the polyol can be prepared prior to alkoxylation and the foregoing structures are intended to encompass compounds prepared in this alternative manner.

The group,

where used herein is derived from alkylene oxide which can be ethylene oxide, propylene oxide, butylene oxide or mixtures of same. Where mixtures of alkylene oxide are added to polyol, the alkoxylated polyol is referred to as heteric. Where two or more of these alkylene oxides are added to polyol sequentially, the alkoxylated polyol is referred to as block. The foregoing structures are intended to encompass such structures.

The radiation hardenable compositions which contain the diluent and oligomer may be hardened or cured by means of high-energy radiation, such as UV-light, electron beams, gamma rays or through chemical and thermal cure mechanisms such as infra-red.

In cases where polymerization is carried out with UV-light, a photocatalyst (photosensitizer or photoinitiator) may be used. Such may be any one of the compounds normally used for this purpose, for example, benzophenone and aromatic keto compounds derived from benzophenone, such as alkyl benzophenones, halogen-methylated benzophenones, Michler's ketone, anthrone and halogenated benzophenones. Other effective photoiniators are anthraquinone and many of its derivatives, for example beta-methyl anthraquinone, tert-butyl anthraquinone and anthraquinone carboxylic acid esters, chlorosulphonated xanthones and thioxanthones and also oxime esters. Other useful photoinitators are benzoin ethers such as benzoin methyl ether, benzoin ethyl ether, benzoin butyl ether, benzil ketals such as benzil and acetophenone derivatives such as diethoxyacetophenone.

The above-mentioned photocatalysts may be used in quantities of from 0.2 to 20 percent by weight, preferably in quantities of from 1 to 10 percent by weight based on the total composition. They may be used either individually or in combination with one another.

Advantageous additives which can produce a further increase in reactivity are certain tertiary and substituted tertiary amines such as triethylamine, 2(n-butoxy)ethyl 4-dimethylamino benzoate, N-methyl diethanolamine and triethanolamine and amine synergists such as aminoacrylates. Additions of phosphines or thioethers are similarly active. The above-mentioned substances are preferably used in quantities of from 0 to 20 percent by weight, based on the total composition.

A description of additional photoinitiators, photosensitizers and amines which can be added to the photosensitizers are set forth in U.S. Pat. No. 4,207,155—Martin et al, Jun. 10, 1980 at column 5, line 49 to column 8, line 10 thereof. This portion of U.S. Pat. No. 4,207,155 is incorporated by reference herein.

Like any system capable of vinyl polymerization, the radiation-hardenable resin compositions have present polymerization inhibitors in order to obtain high stability in storage. These are well known in the art and can be the same as those previously enumerated in connection with the esterification reaction whether introduced during esterification or afterwards. The quantity to be added is determined by the required degree of stabilization and also by the acceptable losses of reactivity which are frequently incurred by the addition of stabilizers. The type and optimum quantity of stabilizer must be determined by concentration tests to be carried out from case to case with varying concentrations of stabilizer. The stabilizers are generally present in quantities of from 0.001 to 0.5 percent by weight, based on the total composition.

If desired, the radiation hardenable compositions may also contain immiscible polymeric or non-polymeric organic or inorganic fillers or reinforcing agents, e.g., the organophilic silicas, bentonites, silica, powdered glass, colloidal carbon as well as various dyes and pigments in varying amounts.

Examples of radiation curable oligomers with which the diluents are used are reaction products of at least one polyepoxide containing more than one 1,2-epoxide group per molecule and acrylic or methacrylic acid or mixtures thereof, about 0.6 to 1 mole of carboxyl groups having been used to one epoxide group. The polyepoxides may be pre-extended (polyfunctional compounds) or modified (monofunctional compounds) with ammonia, aliphatic or cycloaliphatic primary or secondary amine, with hydrogen sulphide, aliphatic, cycloaliphatic, aromatic or aliphatic dithiols or polythiols, with dicarboxylic acid and polycarboxylic acids, from 0.01 to 0.6 NH or SH or COOH equivalents per one epoxide equivalent. The reaction products described above may optionally have been modified with isocyanates. Also epoxidized natural oil acrylates such as epoxidized linseed oil acrylate and epoxidized soya acrylate may be used.

The radiation-hardenable compositions also include unsaturated polyesters which contain radiation-hardenable saturated and unsaturated carboxylic acids, such as maleic acid, fumaric acid and adipic acid in co-condensed form such as a copolymer of adipic and acrylic acid.

Reaction products of diisocyanates and polyisocyanates with hydroxy alkyl acrylates and methacrylates can be used as well as other urethanes containing acrylic and methacrylic acid units. An example is a toluene diisocyanate based acrylate compound. Also other useful oligomers are based on bisphenol A type compounds such as the diglycidyl ether of bisphenol A diacrylate.

The oligomers useful herein are well known materials and the invention is not limited to any particular radiation curable oligomer or mixture of oligomers.

The diluents or mixtures thereof according to the invention may be present in the radiation hardenable compositions in a proportion of from 5 to 80 percent by weight and preferably in a proportion of from 10 to 70% by weight based on the total mixture.

The radiation hardenable compositions produced with the diluents according to the invention are suitable for use as coating and impregnating compositions for wood, paper, cardboard, plastics, leather, metals, fibers, textiles, concrete, ceramic materials, plaster and glass. These compositions may also be used as binders for printing inks, photoresists for the production of screen printing forms, screen printing compositions, adhesives for pressure sensitive tapes, decals and laminates.

Other applications for the radiation hardenable compositions containing the improved diluents described herein are photopolymer plates and reproduction films in the graphic arts, barrier coatings in packaging, flooring, furniture and appliances in consumer applications, conductive coatings and electrical insulation, as printed circuit inks, photoresists, wire coatings and encapsulation/conformal coatings in electronics and fiber optics, magnetic tapes, dielectric coatings and wire-coil bonding in communications.

The radiation hardenable compositions can be applied to the materials to be coated or impregnated by conventional means including brushing, spraying, dipping, curtain and roll coating techniques and if desired dried under ambient or oven conditions.

TEST METHODS

The test methods used in collecting the data herein are described below.

Adhesion

Follows the standard ASTM D 3359-78 procedure using the cross-hatch method with #600 Cellotape giving 40 pound per linear inch pull up where the degree of adhesion is a measure of the amount of film left on substrate after the tape is removed from the etched area. The degree of adhesion is measured on a scale of 0–100%.

Scuff Resistance

An arbitrary measurement using a fingernail and is measured by the resistance to tearing of the coating. This is done by running a fingernail at a 90° angle to the film several times.
G=Good-no marking of film
F=Fair-slight marking
P=Poor-penetration and tearing of film Solvent Resistance Use methylethyl ketone (MEK) as test solvent. Numbers signify the amount of rubs (1 rub=one back and forth motion) with a cotton swab soaked with methylethyl ketone required to etch and penetrate film.

Percent Elongation, Tensile Strength and Tensile Modulus

Wet films of 2.52 mils are prepared using a number 28 RDS rod. Coatings are then cured at 100 ft/min. until a non-tacky coating is obtained.

Films 4 inches long and ¼ inch wide are then cut and removed from substrate. Average film thickness is then determined using a micrometer.

Samples are then placed in an Instron Universal Tester, Model TTD using 200 pound cell, with clamp distances being two inches. Samples are run and measurements for tensile strength, percent elongation and tensile modulus are calculated from chart.

Cure Rate

Using a Fusion Systems ultraviolet curing machine Model No. F440, samples are cured with a 300 watt-/inch bulb suspended two inches from the substrate at 100 feet/minute line speed. Samples are repeatedly passed through the machine until a non-tacky, scuff resistant film is obtained.

Pencil Hardness

Use standard pencil hardness kit from Gardner Laboratories with lead ranging from 4B, the softest, to 6H, the hardest. Follow standard ASTM D 3363-74 procedure for testing coatings.

Gloss

Gloss is determined by using a 60° gloss meter
G=Good—85-100%
F=Fair—less than 85%

Shrinkage

Shrinkage of cured films is done following ASTM procedures (D-792). Approximately 1 to 2 grams of cured product is used for shrinkage determinations.

Color

Where Lumetron readings are given, a Lumetron Colorimeter, Model No. 401 was used.

Conical Mandrel

Cured samples on the test substrate are placed in the mandrel which is calibrated from 0.25 inches to 1.5 inches. The substrate with the coating is bent around the mandrel and observed for cracks. The data reported is where a crack is first observed and this data can be used to determine flexibility of the coating.

For a fuller understanding of this invention, reference may be made to the following examples. These examples are given merely to illustrate the invention and are not to be construed in a limiting sense.

EXAMPLE I

Mono-methoxy 1,6-hexanediol monoacrylate (A) Preparation of 1,6-hexanediol monomethyl ether Hexanediol was melted and 1,025.7 grams charged to a prewarmed pressure reactor (1 liter capacity). The top was sealed and 174 grams caustic soda was added through the charging port with stirring and a slight nitrogen sparge at 60° C.

Heating was continued to 100° C. Then the sparge discontinued and full vacuum applied for 30 minutes. The reaction was then cooled to 89° C., pressured with nitrogen to 5 psig and 220 grams methyl chloride added slowly. Pressure was maintained below 50 psig throughout addition. Temperature was reduced with cooling during the addition to 70° C. When addition was complete, the reaction was allowed to continue until a constant pressure for one hour was reached.

160.7 grams caustic soda were then added and methyl chloride addition continued until 244 grams of additional methyl chloride were added. Reaction was allowed to continue until a constant pressure was reached as before.

Then 857.4 grams of tap water was added with stirring and the reactor heated to 100° C. The contents were poured into a separatory funnel, and the bottom water layer discarded. The reaction product was then stripped to less than 0.2% water, and filtered at 60° C. The clear, yellow liquid had a viscosity of 12.5 cps, Gardner 1 color, and hydroxyl number of 508.

(B) Preparation of 1,6-hexanediol monomethyl ether acrylate 803.6 grams of the monomethyl ether described in Part (A) above were azeotropically esterified with 629.8 grams acrylic acid in 254.6 grams toluene in the presence of 24 grams p-toluenesulfonic acid and inhibitors until no more water was collected. Conditions were 95°–98° C., nitrogen sparge in vacuo. On completion, the product was washed and neutralized with sodium carbonate. 900 ppm p-methoxyphenol (MEHQ) was added and the solvent removed at 80° C. with maximum vacuum in the presence of an air sparge. Filter aid was added and the product filtered at 60° C. to give a clear, yellow liquid having a viscosity of 6.5 cps and a Gardener color of 3. Equipment used was a 2 liter flask, thermometer, Dean-Stark condenser and sparge tube.

EXAMPLE II

Mono-methoxy diethylene glycol monoacrylate 682 grams Methyl Carbitol (diethylene glycol monomethyl ether, Union Carbide) were azeotropically esterified with 598.9 grams acrylic acid in 272 grams toluene in the presence of 22.8 grams p-toluenesulfonic acid and inhibitors until no more water was collected. Conditions were 95°–98° C., nitrogen sparge in vacuo. On completion, the product was washed and neutralized with sodium carbonate. 1,300 ppm p-methoxyphenol were added and solvent removed at 80° C. at maximum vacuum with an air sparge. Filter aid was added and the product filtered to clarity at 50° C. The final product was a clear, light yellow liquid, viscosity 6 cps with a Gardner 1 color.

Equipment used was a 2 liter flask, thermometer, Dean-Stark condenser and sparge tube.

EXAMPLE III

Diethylene glycol monobutyl ether acrylate 300.1 grams Dowanol DB (diethylene glycol monobutyl ether, Dow Chemical Company) were azeotropically esterified at 95°–98° C. using nitrogen sparge and vacuum with 158.7 grams acrylic acid in 93.3 grams toluene in the presence of 9 grams p-toluenesulfonic acid and inhibitors until no more water was collected. On completion, the product was washed and neutralized with sodium carbonate. 1,000 ppm p-methoxyphenol were added and the solvent removed at 80° C. with maximum vacuum and air sparge. Filter aid was added and a clear, yellow liquid obtained at 60° C. Viscosity was 5.5 cps with a Gardner 1 color. Equipment used was a 500 ml flask, thermometer, Dean-Stark condenser and sparge tube.

EXAMPLE IV

Ethylene glycol monopropyl ether acrylate

Using the conditions and equipment of Example III, ethylene glycol monopropyl ether acrylate was prepared from the following:

| Materials | Weight (grams) |
|---|---|
| ethylene glycol monopropyl ether (Eastman Chemicals) | 240.00 |
| toluene | 113.10 |
| p-toluenesulfonic acid | 9.95 |
| inhibitors | 0.22 |
| acrylic acid | 202.40 |

Product was washed and neutralized with sodium carbonate. 700 ppm methyl ether of hydroquinone (MEHQ) was added and product filtered to clarity at 70° C. Product was a light yellow liquid having a viscosity of 3.5 cps and a Gardner 1 color.

EXAMPLE V

Mono-methoxy, ethoxylated neopentyl glycol monoacrylate having an average of two moles of ethylene oxide (A) Preparation of neopentyl glycol having an average of two moles of ethylene oxide The following procedure was followed, although larger quantities of reactants were used in order to prepare the amount used in part (B).

54.09 grams of neopentyl glycol and 0.2 gram of caustic potash were charged to a reaction flask equipped with stirrer, thermometer and gas inlet pipes and heated to 130° C. Then 45.71 grams of ethylene oxide were added slowly. On completion, the product was cooled and filtered. The final product obtained had a maximum Gardner of 2 and a hydroxyl number of 556–560.

(B) Preparation of mono-methoxy, ethoxylated neopentyl glycol having an average of two moles of ethylene oxide Using the procedure of Example I (A), mono-methoxy, ethoxylated neopentyl glycol having an average of two moles of ethylene oxide was prepared from the following:

| Material | Amount (gms.) |
|---|---|
| neopentyl glycol having an average of two moles of ethylene oxide from part (A) | 650.8 |
| sodium hydroxide | 128.5 (introduced in two portions) |
| methyl chloride | 163.0 (introduced in two portions) |

Product had a hydroxyl number of 273.0, a Brookfield viscosity of 17.5 cps (No. 1 spindle at 60 rpm at 24° C.) and was a clear, yellow liquid. The color, based on a Lumetron reading using a No. 420 filter was 89.5.

(C) Preparation of mono-methoxy, ethoxylated neopentyl glycol monoacrylate having an average of two moles of ethylene oxide Using the procedure of Example II, mono-methoxy, ethoxylated neopentyl glycol monoacrylate having an average of two moles of ethylene oxide was prepared from the following:

| Material | Amount (gms.) |
|---|---|
| mono-methoxy, ethoxylated neopentyl glycol having an average of two moles of ethylene oxide from part (B) | 487 |
| toluene + inhibitors | 309 |
| p-toluenesulfonic acid | 17.4 |
| acrylic acid | 171 |

The product was a clear, yellow liquid with a Brookfield viscosity of 9.7 cps (No. 2 spindle at 60 rpm at 25° C. The color, based on a Lumetron reading using a No. 420 filter was 82.

EXAMPLE VI

Mono-methoxy, propoxylated neopentyl glycol monoacrylate having an average of two moles of propylene oxide (A) Preparation of neopentyl glycol having an average of two moles of propylene oxide The following procedure was followed although larger quantities of reactants were used in order to prepare the amount used in part (B).

44.8 grams of neopentyl glycol were charged to a reaction flask equipped with stirrer, thermometer and gas inlet pipes and heated to melt. Then, 0.2 gram of caustic potash was added followed by slow addition of 55 grams of propylene oxide. On completion, the product was stripped and cooled. The final product was a clear, light liquid having a hydroxyl number of 483–490 and a Gardner color of 2.

(B) Preparation of mono-methoxy, propoxylated neopentyl glycol having an average of two moles of propylene oxide Using the procedure of Example I (A), mono-methoxy, propoxylated neopentyl glycol having an average of two moles of propylene oxide was prepared from the following:

| Material | Amount (gms.) |
|---|---|
| neopentyl glycol having an average of two moles of propylene oxide from part (A) | 705.5 |
| sodium hydroxide | 128.8 (introduced in two portions) |
| methyl chloride | 162.5 (introduced in two portions) |

The product was a clear, water white liquid having a hydroxyl number of 290.3 and a Brookfield viscosity of 18 cps (No. 1 spindle at 60 rpm at 24° C.). Color, based on a Lumetron reading using a No. 420 filter was 99.5.

(C) Preparation of mono-methoxy, propoxylated neopentyl glycol monoacrylate having an average of two moles of propylene oxide Using the procedure of Example II, mono-methoxy, propoxylated neopentyl glycol monoacrylate having an average of two moles of propylene oxide was prepared as follows:

| Material | Amount (gms.) |
| --- | --- |
| mono-methoxy, propoxylated neopentyl glycol having an average of two moles of propylene oxide from part (B) | 668.7 |
| toluene + inhibitors | 383.7 |
| p-toluenesulfonic acid | 24.9 |
| acrylic acid | 274.5 |

The product was a light, yellow liquid having a Brookfield viscosity of 5 cps (No. 1 spindle at 60 rpm at 23.5° C.). Color, based on a Lumetron reading using a 420 filter was 87.

region. This point of the spectrum was selected as there appeared to be minimal interference from other functional groups.

Measurements were made on a polished sodium chloride plate coated with a wet monomer layer approximately seven microns thick. The coatings (with photocatalyst) were then subjected to short exposures of UV radiation with residual double bond measurements taken after each exposure. This procedure was repeated until the vinyl peak in the spectrum reached a constant level.

The results of a comparative photocure study of selected monomers analyzed by infra-red is presented in Table I below.

In Table I, per cent residual unsaturation was determined by monitoring decrease of the infra-red absorption of the reactive vinyl double bond as stated above. Cure time values were converted from cure speed. Cure speed was determined from number of cure passes, each pass made at 100 feet per minute.

TABLE I
Photoreactivity Comparison Between Selected Acrylates and their Monomethyl Ether Derivatives

| Compound | Acrylate Functionality | % Residual Unsatn | Cure Time (Millisec) | Cure Speed (Ft/min) | Cure Passes (No.) | Relative Reactivity |
| --- | --- | --- | --- | --- | --- | --- |
| Trimethylolpropane triacrylate | 3 | 22 | 60 | 3 | 33 | 1 |
| Mono-methoxy trimethylolpropane diacrylate | 2 | 16 | 14 | 14 | 7 | 4 |
| Ethoxylated (3 moles) trimethylolpropane triacrylate | 3 | 18 | 6 | 33 | 3 | 10 |
| Mono-methoxy ethoxylated (3 moles) trimethylolpropane diacrylate | 2 | 10 | 6 | 33 | 3 | 10 |
| Propoxylated (3 moles) trimethylolpropane triacrylate | 3 | 16 | 10 | 20 | 5 | 6 |
| Mono-methoxy propoxylated (3 moles) trimethylolpropane diacrylate | 2 | 6 | 10 | 20 | 5 | 6 |
| 1,6-Hexanediol diacrylate | 2 | 14 | 60 | 3 | 33 | 1 |
| Mono-methoxy 1,6-hexanediol monoacrylate | 1 | 3 | 16 | 12 | 8 | 4 |

Cure Conditions: Benzophenone 6% by weight of acrylate; one 300 watt/inch Fusion H Lamp (mercury), 7 Micron Neat Wet Film, Polished Sodium Chloride Plates

EXAMPLE VII

In this example, a comparison was carried out on the photoreactivity of a group of monomers within the scope of this invention and their parent compounds which, of course, contained an additional acrylate group in place of the ether group.

To establish relative cure speed of a monomer, its UV cured films (homopolymers) were tested to ensure that optimum surface and through cure conditions were achieved. Cure speed is defined as the time required to generate a coating (film) from a monomer that is thumb, tack and scratch resistant as measured by scuff and pencil hardness tests. These conditions correlate well with wet films coated on sodium chloride plates, cured by UV and analyzed by infra-red.

This non-destructive technique, i.e., infra-red analysis, was utilized to further establish the cure rate of each monomer and its relationship to the degree or extent of conversion of double bonds to homopolymers. For each reactive monomer, there is an inherent unsaturation level, i.e., unreacted double bonds, that is reached beyond which no further apparent reduction in unsaturation is observed.

The extent of UV cure (photopolymerization) of monomers to homopolymers was monitored by decrease of infra-red absorption of the reactive vinyl double bond in the acrylate group in the 810–820 cm$^{-1}$ In the trimethylolpropane triacrylate family, a definitive increase in reactivity and completeness of cure under the conditions of the study was observed. In every derivative of trimethylolpropane triacrylate and its methyl ether analog, the methyl ether acrylate cured more completely and no slower than its related parent as reflected by cure time and residual unsaturation. On a relative reactivity basis, the following order was observed (fastest to slowest) with benzophenone:

As the data suggests, there was no loss in reactivity (cure response) in the monomers by substituting a methoxy group for an acrylate group. Monomers with the methoxy group were essentially equivalent or faster in cure speed under the test conditions. Similarly, 1,6-hexanediol diacrylate and its methyl ether analog exhibited the same increase in cure and completeness of cure. Thus, modification of an acrylate monomer with an ether group resulted in a derivative monomer with at least the same cure response, i.e., a difunctional acrylate cured at least as fast as its trifunctional parent, which was most unusual and unexpected. For example, TMPME(EO)₃DA was equivalent in cure to TMP(EO)₃TA, both of which cured ten times as fast as trimethylolpropane triacrylate.

EXAMPLE VIII

In this example, a number of lower alkyl ether ethoxylated and non-ethoxylated acrylates were evaluated with topical and bulk photoinitiators or catalysts. The cure rates are reported as cure speeds (feet/min.). Per cent by weight of catalyst is per cent by weight of total of catalyst plus monomer. The data is set forth in Table II.

Listed below are the abbreviations for the compounds appearing in Table II. Where repeated, these abbreviations will have the same meaning.

| | |
|---|---|
| PETA | pentaerythritol triacrylate |
| PE(PO)₄TA | propoxylated (4 moles) pentaerythritol triacrylate |
| PEME(PO)₄TA | mono-methoxy propoxylated (4 moles) pentaerythritol triacrylate |
| TMPTA | trimethylolpropane triacrylate |
| TMP(EO)₃TA | ethoxylated (3 moles) trimethylol propane triacrylate |
| TMPME(EO)₃DA | mono-methoxy, ethoxylated (3 moles) trimethylolpropane diacrylate |
| TMP(PO)₃TA | propoxylated (3 moles) trimethylol propane triacrylate |
| TMPME(PO)₃DA | mono-methoxy propoxylated (3 moles) trimethylolpropane diacrylate |
| HDODA | 1,6-hexanediol diacrylate |
| HDOMEMA | mono-methoxy 1,6-hexanediol mono-acrylate |
| TRPGDA | tripropylene glycol diacrylate |
| TRPGMEMA | mono-methoxy tripropylene glycol monoacrylate |
| NPGDA | neopentyl glycol diacrylate |
| NPG(EO)₂DA | ethoxylated (2 moles) neopentyl glycol diacrylate |
| NPGME(EO)₂MA | mono-methoxy ethoxylated (2 moles) neopentyl glycol monoacrylate |
| NPG(PO)₂DA | propoxylated (2 moles) neopentyl glycol diacrylate |
| NPGME(PO)₂MA | mono-methoxy propoxylated (2 moles) neopentyl glycol monoacrylate |
| DEGMEMA | mono-methoxy diethylene glycol mono-acrylate |
| EGPEMA | mono-propoxy ethylene glycol mono-acrylate |
| CHDMEMA | mono-methoxy trans-1,4-cyclohexane dimethylol monoacrylate |
| DEGBEMA | mono-n-butoxy diethylene glycol mono-acrylate |
| DEGEEMA | mono-ethoxy diethylene glycol mono-acrylate |

TABLE II

Photoreactivity Evaluation Cure Speed (Feet/Min)

| Compound | Acrylate Functionality | Photocatalyst 6% BP by wt. | 6% BP by wt. 2% TEOA by wt. | 4% by wt. Irgacure 651 |
|---|---|---|---|---|
| PETA | 3 | 7 | 33 | 12 |
| PE(PO)₄TA | 3 | 25 | 33 | 4 |
| PEME(PO)₄TA | 3 | 25 | 25 | 3 |
| TMPTA | 3 | 2 | 7 | 5 |
| TMP(EO)₃TA | 3 | 25 | 33 | 5 |
| TMPME(EO)₃DA | 2 | 20 | 20 | 4 |
| TMP(PO)₃TA | 3 | 17 | 25 | 3 |
| TMPME(PO)₃DA | 2 | 14 | 20 | 2 |
| HDODA | 2 | 2 | 5 | 2 |
| HDOMEMA | 1 | 8 | 8 | 4 |
| TRPGDA | 2 | 13 | 16 | 2 |
| TRPGMEMA | 1 | 10 | 10 | 2 |
| NPGDA | 2 | 2 | 3 | 2 |
| NPG(EO)₂DA | 2 | 20 | 20 | 3 |
| NPGME(EO)₂MA | 1 | 7 | 7 | 2 |
| NPG(PO)₂DA | 2 | 14 | 16 | 2 |
| NPGME(PO)₂MA | 1 | 14 | 12 | 5 |
| DEGMEMA | 1 | 5 | 5 | 5 |
| EGMEMA | 1 | 4 | 4 | 1 |
| CHDMEMA | 1 | 17 | 20 | 4 |
| DEGBEMA | 1 | 4 | 4 | 7 |
| DEGEEMA | 1 | 4 | 10 | 3 |

Cure conditions: One 300 watt/inch Fusion H Lamp (Mercury); 0.27 mil wet film Aluminum Substrate
BP = benzophenone
TEOA = triethanolamine
Irgacure 651 = 2,2-dimethoxy-2-phenyl acetophenone With benzophenone, the data is consistent with that of Table I. The parent acrylates, i.e., those not containing an ether group consistently exhibited the slowest cure response. In some instances, the reactivity of the methyl ether alkoxylated acrylate analogs was not as quite as high as their precursors due to some unknown influence of the substrate. Several of the monofunctional ether acrylates generated relatively fast cure responses. This is most surprising as typical monofunctional acrylates are slow curing, forming tacky coatings with little integrity and almost no crosslink character.

Addition of an amine hydrogen donor to benzophenone (topical cure type) either increased the apparent cure speed or had no effect. Thus, the amine hydrogen donor can be eliminated when the monomers of this invention are used in topical cures. With Irgacure 651 (bulk cure type), there were essentially no significant differences among mono-, di-, and tri-functional types. Although, they are all slow curing, with the exception of pentaerythritol triacrylate, the methyl ether acrylate analog cured no slower than its related parent in most cases. Apparently, oxygen inhibition severely affects their reactivity.

In addition to reactivity, radiation curable diluents, as pointed out above, contribute to the final properties of the cured film. That is, they may modify or influence important properties of the oligomers in the cured coating such as hardness, flexibility, shrinkage, tensile strength and elongation. These properties are important parameters for coating materials since they influence the ultimate application of the coating materials. Tables III, IV and V below detail these properties with respect to the radiation hardenable diluents. Quantities of photocatalyst are per cent by weight of monomer.

Listed below are abbreviations of additional compounds not heretofore set forth.

| | |
|---|---|
| PEMETA | mono-methoxy pentaerythritol triacrylate |
| TMPMEDA | mono-methoxy trimethylolpropane diacrylate |
| NPGMEMA | mono-methoxy neopentyl glycol monoacrylate |

TABLE III

Selected Properties
Acrylate Monomers & Benzophenone (6%)
Aluminum Substrate

| Compound | Scuff Resist | Gloss 60° | MEK Rubs | Pencil Hard | % Adhes (X-Hatch) | % Shrink | % Elong | Ten Str (psi) | Tens Mod (psi) × 10⁴ |
|---|---|---|---|---|---|---|---|---|---|
| PETA | G | G | 100 | H | 0 | 28 | — | — | — |
| PEMETA | G | G | 38 | H | 0 | — | — | — | — |
| PE[PO]₄TA | G | G | 100 | H | 0 | 17 | 3.9 | 626 | 1.6 |
| PEME[PO]₄TA | G | G | 10 | 2B | 0 | 15 | 5.7 | 550 | 1.0 |
| TMPTA | G | G | 100+ | F | 0 | 26 | — | — | — |
| TMPMEDA | G | G | 25 | F | 0 | — | — | — | — |
| TMP[EO]₃TA | G | G | 100+ | F | 0 | 24 | 1.0 | 962 | 9.6 |
| TMPME[EO]₃DA | F/G | G | 30 | 4B | 0 | 19 | 5.5 | 939 | 1.7 |
| TMP[PO]₃TA | G | G | 100+ | F | 0 | 15 | 1.7 | 1167 | 6.8 |
| TMPME[PO]₃DA | G | G | 100+ | B | 0 | 6 | 5.2 | 362 | 0.7 |
| HDODA | G | G | 100+ | F | 0 | 14 | 1.1 | 291 | 2.9 |
| HDOMEMA | G | G | 10 | 4B | 0 | 8 | — | — | — |
| TRPGDA | G | G | 100+ | BH | 0 | 16 | 4.4 | 347 | 0.8 |
| TRPGMEMA | P | — | 3 | 4B | 100 | — | — | — | — |
| NPGDA | G | G | 100+ | 4H | 0 | 9 | — | — | — |
| NPGMEMA | G | G | 5 | H | 0 | — | — | — | — |
| NPG[EO]₂DA | G | G | 100+ | 2B | 0 | 14 | — | — | — |
| NPGME[EO]₂MA | E | G | 10 | B | 12 | 8 | — | — | — |
| NPG[PO]₂DA | G | G | 100 | F | 0 | 6 | 6.5 | 1084 | 1.7 |
| NPGME[PO]₂MA | P | — | 5 | 4B | 90 | 3 | — | — | — |
| DEGMEMA | P | — | 10 | 4B | 100 | — | — | — | — |
| CHDMEMA | G | G | 19 | H | 0 | 8 | — | — | — |

TABLE IV

Selected Properties
Acrylate Monomers & Benzophenone (6%)/TEOA (2%)
Aluminum Substrate

| Compound | Scuff Resist | Gloss 60° | MEK Rubs | Pencil Hard | % Adhes (X-Hatch) | % Shrink | % Elong | Ten Str (psi) | Tens Mod (psi) × 10⁴ |
|---|---|---|---|---|---|---|---|---|---|
| PETA | G | G | 100 | H | 0 | 28 | — | — | — |
| PEMETA | G | G | 39 | H | 0 | — | — | — | — |
| PE[PO]₄TA | G | G | 100+ | H | 0 | 17 | 2.7 | 632 | 2.4 |
| PEME[PO]₄TA | G | G | 100+ | H | 0 | 17 | 4.5 | 499 | 1.1 |
| TMPTA | G | G | 100+ | F | 16 | 24 | — | — | — |
| TMPMEDA | G | G | 18 | F | 0 | — | — | — | — |
| TMP[EO]₃TA | G | G | 100+ | F | 0 | 14 | 2.2 | 1196 | 5.6 |
| TMPME[EO]₃DA | G | G | 30 | 4B | 0 | 6 | — | — | — |
| TMP[PO]₃TA | G | G | 100 | F | 8 | 15 | 3.4 | 1422 | 4.3 |
| TMPME[PO]₃DA | G | G | 30 | 4B | 0 | 5 | 3.7 | 205 | 0.6 |
| HDODA | G | G | 100+ | F | 0 | 20 | 1.1 | 640 | 5.4 |
| HDOMEMA | F/G | G | 9 | 4B | 0 | 9 | — | — | — |
| TRPGDA | G | G | 100+ | BH | 12 | 11 | 4.5 | 633 | 0.4 |
| TRPGMEMA | P | — | 3 | 4B | 100 | — | — | — | — |
| NPGDA | G | G | 100+ | H | 0 | 16 | — | — | — |
| NPGMEMA | G | G | 5 | H | 0 | 10 | — | — | — |
| NPG[EO]₂DA | G | G | 100+ | F | 32 | 15 | 4.7 | 253 | 0.5 |
| NPGME[EO]₂MA | F | G | 11 | 4B | 0 | 10 | — | — | — |
| NPG[PO]₂DA | G | G | 100+ | F | 0 | 14 | 4.7 | 583 | 1.3 |
| NPGME[PO]₂MA | F | G | 2 | 4B | 64 | 6 | — | — | — |
| DEGMEMA | P | G | 9 | 4B | 100 | — | — | — | — |
| CHDMEMA | G | G | 23 | 2B | 0 | — | — | — | — |

TABLE V

Selected Properties
Acrylate Monomers & Irgacure 651 (4%)
Aluminum Substrate

| Compound | Scuff Resist | Gloss 60° | MEK Rubs | Pencil Hard | % Adhes (X-Hatch) | % Shrink | % Elong | Ten Str (psi) | Tens Mod (psi) × 10⁴ |
|---|---|---|---|---|---|---|---|---|---|
| PETA | G | G | 100+ | H | 0 | 33 | — | — | — |
| PEMETA | — | — | — | — | — | — | — | — | — |
| PE[PO]₄TA | G | G | 100+ | 2H | — | 18 | 1.3 | 1319 | 10.6 |
| PEME[PO]₄TA | G | G | 100+ | 2H | — | 14 | 2.5 | 1623 | 6.6 |
| TMPTA | G | G | 100+ | 3H | 8 | 25 | — | — | — |
| TMPMEDA | — | — | — | — | — | — | — | — | — |
| TMP[EO]₃TA | G | G | 100+ | 3H | 0 | 17 | 1.0 | 1357 | 13.6 |
| TMPME[EO]₃DA | F | G | 50 | H | 0 | 13 | 5.5 | 385 | .7 |
| TMP[PO]₃TA | F | G | 100+ | 2H | 4 | 12 | 1.4 | 1316 | 9.8 |
| TMPME[PO]₃DA | F | G | 100+ | 2H | 12 | 8 | 2.1 | 1686 | 7.9 |
| HDODA | G | G | 100+ | 2H | 0 | 9 | 1.0 | 1401 | 14.0 |
| HDOMEMA | F | G | 7 | H | 32 | 5 | — | — | — |
| TRPGDA | F | G | 100+ | 2H | 0 | 14 | 2.4 | 2324 | 5.0 |

TABLE V-continued

Selected Properties
Acrylate Monomers & Irgacure 651 (4%)
Aluminum Substrate

| Compound | Scuff Resist | Gloss 60° | MEK Rubs | Pencil Hard | % Adhes (X-Hatch) | % Shrink | % Elong | Ten Str (psi) | Tens Mod (psi) × $10^4$ |
|---|---|---|---|---|---|---|---|---|---|
| TRPGMEMA | P | G | 3 | 4B | 60 | — | — | — | — |
| NPGDA | F/G | G | 100 | F | 0 | 14 | 3.5 | 1348 | 7.4 |
| NPGMEMA | — | — | — | — | — | — | — | — | — |
| NPG[EO]$_2$DA | G | G | 100+ | H | 0 | 15 | 6.0 | 2170 | 3.8 |
| NPGME[EO]$_2$MA | F | G | 5 | 4B | 8 | 11 | — | — | — |
| NPG[PO]$_2$DA | F/G | G | 100 | H | 0 | 8 | 2.9 | 3242 | 11.3 |
| NPGME[PO]$_2$MA | F | G | 4 | 4B | 0 | 6 | — | — | — |
| DEGMEMA | P | G | 4 | 4B | 100 | — | — | — | — |
| CHDMEMA | F | G | 35 | BH | 0 | 8 | 0.9 | 359 | 4.0 |

Referring to the data of Tables III, IV and V, for all photocatalysts studied, there were no dramatic differences in gloss or scuff resistance of the homopolymers made from the methoxy acrylates over the parent monomers. However, for MEK resistance and pencil hardness (broad measures of solvent resistance, crosslink density and completeness of cure), there were significant changes observed. In every derivative series tested (e.g. TMP family), the MEK resistance either was unchanged or dramatically reduced. This was not entirely unexpected since the presence of lower alkyl ether reduces the functionality (acrylate group) of the derivatives by one. Hence, the methoxy acrylates would exhibit lower crosslink density and lower solvent resistance. The only exceptions were TMPME(PO)$_3$DA and PEME(PO)$_4$TA.

Pencil hardness also reflected lower crosslink density resulting from this modification. In each derivative series tested, the pencil hardness was unchanged or reduced in ratings. Overall, UV cured films of methoxy acrylates generated softer hardness ratings than the parent acrylates.

Regarding adhesion to aluminum, several of the methoxy acrylates exhibited varying degrees of adhesion ranging from 12-100% based on cross-hatch studies with Cellotape #600. Past experience has shown that good to excellent adhesion of reactive monomers to metals and plastics is very difficult to achieve because of surface energy differences, substrate hydrophobicity, high shrinkage on cure and high crosslink density. The reactive monomers that developed good to excellent adhesion were TRPGMEMA, NPGME(PO)$_2$MA and DEGMEMA, all monofunctional methoxy acrylates. Several other methoxy acrylates and regular acrylates also demonstrated some adhesive character ranging from poor to moderate.

As indicated previously, a reactive monomer property that is particularly important in developing good adhesion is film shrinkage of the homopolymer on curing.

In every derivative series tested, the methoxy acrylate analogs exhibited the lowest film shrinkage on cure. Overall, propoxylated methoxy acrylates generated lower shrinkage values than did the corresponding ethoxylated methoxy acrylate analogs. These lower shrinkage values may reflect the combined affects of reduced functionality and lower crosslink density.

The mechanical characteristics of the homopolymers derived from the presence of lower alkyl ether acrylate monomers, such as tensile strength and elongation, generally mirror the lower crosslink networks inherent in their structures. In general, the methoxy acrylates produced higher elongation values (i.e., they were more flexible), and lower tensile strength than did the parent acrylate. No meaningful data could be produced from the monofunctional types as they are not film formers. These monomers function primarily as reactive diluents, i.e., they are viscosity reducers, and contribute marginally to the mechanical properties of the finished UV curable coating, ink or adhesive.

The fact that lower alkyl ether acrylate derivatives of various polyols produce compounds of lower viscosity than the parent acrylates is generally supported by experimental data. Table VI is a comparison of a number of acrylate monomers and their derivative methyl ether acrylates.

TABLE VI

Neat Viscosity Comparison
Acrylates vs. Methoxy Acrylate Derivatives
Brookfield, Spindle 1-4, 60 RPM, 25° C.

| Acrylate | Viscosity (cps) | Methoxy Acrylate | Viscosity (cps) |
|---|---|---|---|
| PETA | 600–800 | PEMETA | 51 |
| PE(PO)$_4$TA | 225 | PEME(PO)$_4$TA | 113–139 |
| TMP(EO)$_3$TA | 70–100 | TMPME(EO)$_3$DA | 29–78 |
| TMP(PO)$_3$TA | 80–110 | TMPME(PO)$_3$DA | 33–36 |
| [1]Gly(PO)$_3$TA | 80–100 | [2]GlyME(PO)$_3$DA | 29 |
| HDODA | 5–12 | HDOMEMA | 5–6 |
| TRPGDA | 10–20 | TRPGMEMA | 7 |
| NPGDA | 10–15 | NPGMEMA | 5 |
| NPG(EO)$_2$DA | 15–20 | NPGME(EO)$_2$MA | 9–10 |
| NPG(PO)$_2$DA | 14–20 | NPEME(PO)$_2$MA | 5–7 |
| DEGDA | 20–25 | DEGMEMA | 15 |

[1]Propoxylated (3 moles) glycerol triacrylate
[2]Mono-methoxy, propoxylated (3 moles) glycerol diacrylate Overall, a significant reduction in neat viscosity (25–60%) occurred with respect to the methoxy acrylate over the parent from which it was derived. The greatest decrease in viscosity was observed in the TMP series where the functionality was reduced from three to two. In difunctional types, viscosity reduction was not as spectacular as the parent acrylates already exhibited lower intrinsic viscosities. However, even in these instances, the lower viscosities are readily apparent.

Note also in Table VI that the reactive monomers of formulas I through IV demonstrate lower intrinsic viscosities than the reactive monomers of formula V. That is, in a comparison of monoacrylates of formulas I through IV with monoacrylates of formula V, the mono-methoxy, alkoxylated neopentyl glycol monoacrylate of formula I has a lower viscosity than the viscosity of mono-methoxy diethylene glycol monoacrylate of formula V. See columns 3 and 4 of Table VI.

Another measure of the utility of reactive diluents is solvating efficiency or reducing power. Although they may exhibit similar neat viscosities, they do not necessarily produce identical solution viscosities in the presence of an equal amount of oligomer.

A number of factors affect the final solution viscosity including the solvating efficiency and neat viscosity of the monomer. Table VII below details the solution viscosities obtained with selected monomers in the presence of a high viscosity epoxy acrylate oligomer, i.e., bis-phenol A diglycidyl ether diacrylate having a neat viscosity of 2,000,000 cps at 25° C.

TABLE VII

Viscosity Reduction Comparison
Selected Acrylates vs. Methoxy Acrylate Derivatives
in Epoxy Acrylate Oligomer*

| Compound | Monomer Viscosity (cps) | Solution Viscosity (cps) |
|---|---|---|
| TMPTA | 75 | 5,450 |
| TMP(EO)$_3$TA | 80 | 3,500 |
| TMPME(EO)$_3$DA | 29 | 3,350 |
| TMP(PO)$_3$TA | 90 | 4,400 |
| TMPME(PO)$_3$DA | 35 | 2,650 |
| HDODA | 10 | 300 |
| HDOMEMA | 6 | 200 |

*Conditions: 47% by wt. Oligomer, 47% by wt. Monomer, 6% by wt. Benzophenone
Brookfield, #4 spindle, at 60 RPM, 25° C.

For the reactive diluents tested, the methoxy ether acrylates were more effective than the parent from which they were derived. When compared against TMPTA, their viscosity reducing characteristics were even more dramatic ranging from 40-50% more efficient with high viscosity epoxy acrylate oligomers. A similar effect was observed with HDODA and its methoxy acrylate analog.

To test the efficacy of the lower alkoxy acrylates, the monomers were evaluated in a formula which is typical of radiation curable systems. In the simplest case, this is comprised of a reactive oligomer, reactive monomer (diluent) and photocatalyst. Table VIII Details the products tested and the experimental conditions employed.

tivity of the system incorporating the methoxy analog was equal to or greater than the parent from which it was derived. There was no loss in scuff or gloss in the methoxy acrylate formulations (Nos. 3 and 5) as was the case with the neat monomer. Pencil hardness ratings and the MEK rubs also mirrored the results previously described for the neat monomers. A similar conclusion can be drawn for HDODA and its methoxy acrylate analog (Nos. 6 and 7).

On balance, the lower alkoxy acrylates in radiation curable mixtures enhance their reactivity compared to standard multifunctional acrylates (e.g. TMPTA), produce tack-free coatings of equivalent durability and solvent resistance, and generate greater intrinsic flexibility (See Table VIII).

As can be seen from all of the data presented, the lower alkyl ether acrylates exhibit excellent cure response, low viscosity, outstanding solvency and require no hydrogen donors to initiate cure with benzophenone. They cure or harden under ultra-violet radiation to tack free homopolymers that exhibit significantly lower shrinkage than other acrylate type monomers. Further, the radiation curable compositions which contain these lower alkyl ether acrylates are also characterized by the enhanced properties shown by the neat monomers.

EXAMPLE IX

Mono-methoxy, propoxylated pentaerythritol trimethacrylate having an average of four moles of propylene oxide (A) Preparation of pentaerythritol having an average of four moles of propylene oxide The following procedure was followed, although larger quantities of reactants were used in order to prepare the amount used in part (B).

25.1 grams of pentaerythritol and 0.3 gram of caustic potash were charged to a reactor flask equipped with stirrer, thermometer and gas inlet pipes and heated to

TABLE VIII

Radiation Curable System
Acrylates vs. Methoxy Derivatives
(Wt. %)

| | Formulations | | | | | | |
|---|---|---|---|---|---|---|---|
| Compound | 1 | 2 | 3 | 4 | 5 | 6 | 7 |
| BPA Diglycidylether Diacrylate Oligomer | 47 | 47 | 47 | 47 | 47 | 47 | 47 |
| TMPTA | 47 | — | — | — | — | — | — |
| TMP(EO)$_3$TA | — | 47 | — | — | — | — | — |
| TMPME(EO)$_3$DA | — | — | 47 | — | — | — | — |
| TMP(PO)$_3$TA | — | — | — | 47 | — | — | — |
| TMPME(PO)$_3$DA | — | — | — | — | 47 | — | — |
| HDODA | — | — | — | — | — | 47 | — |
| HDOMEDA | — | — | — | — | — | — | 47 |
| Benzophenone | 6 | 6 | 6 | 6 | 6 | 6 | 6 |
| Properties | | | | | | | |
| Cure Speed (Ft/Min) | 20 | 40 | 40 | 25 | 30 | 11 | 30 |
| Scuff | Excl | Excl | Excl | Excl | Excl | Excl | Excl |
| Gloss | Good | Good | Good | Good | Good | Good | Good |
| Pencil Hardness | 5H | 4H | 5H | 5H | 4H | 5H | 5H |
| MEK Rubs | 100 | 100 | 90 | 100 | 100 | 80 | 25 |
| Conical Mandrel (in) | .75" | .25" | .25" | .40" | .25" | .25" | .25" |

Conditions: Aluminum panels (Q-Panel Corp); One 300 watt inch Mercury Lamp; 0.27 Wet Mil Film; RDS #3 Rod; 100 ft/min.
BPA Diglycidylether = Bisphenol A diglycidylether diacrylate having a neat viscosity of 2,000,000 cps at 25° C.

The properties generated from the foregoing UV coating compositions unequivocally support the results generated from comparable studies conducted on the neat monomers. In the TMP family, for example, reac- 85°-90° C. Then 50.8 grams of propylene oxide were added. On completion, the product was cooled and filtered. The final product obtained had a maximum APHA <25 and a hydroxyl number of 550±10.

(B) Preparation of mono-methoxy, propoxylated pentaerythritol having an average of four moles of propylene oxide Approximately 851.7 grams of propoxylated pentaerythritol having an average of four moles of propylene oxide were charged to a prewarmed pressure reactor. The top was sealed and 41.1 grams caustic soda was added through the charging port with stirring and a slight nitrogen sparge at 60° C. The reaction was then heated to approximately 70° C., pressured with nitrogen to 5 psig and 51.9 grams methyl chloride added slowly. Pressure was maintained below 50 psig throughout addition. Temperature was maintained with cooling during the addition to 70° C. When addition was complete, the reaction was allowed to continue until a constant pressure for one hour was reached.

41.1 grams caustic soda were then added and methyl chloride addition continued until 60 grams of additional methyl chloride were added. Reaction was allowed to continue until a constant pressure was reached as before.

Then 514 grams of tap water were added with stirring and the reactor heated to 100° C. The contents were poured into a separatory funnel and the bottom water layer discarded. The reaction product was then stripped to less than 1% water, and filtered at 70° C. The clear yellow liquid had a viscosity of 435 cps, Gardner 2 color and hydroxyl number of 435.

(C) Preparation of mono-methoxy, propoxylated pentaerythritol trimethacrylate having an average of four moles of propylene oxide 154.4 grams of the monomethyl ether described in part (B) above were azeotropically esterified with 169.4 grams methacrylic acid in 56.1 grams toluene in the presence of 11.5 g p-toluenesulfonic acid and inhibitors until no more water was collected. Conditions were 95°-98° C., nitrogen sparge in vacuo. On completion, the product was washed and neutralized with sodium carbonate. 1,000 ppm p-methoxyphenol (MEHQ) were added and solvent removed at 80° C. with maximum vacuum in the presence of an air sparge. Filter aid was added and the product filtered at 60° C. to give a clear, yellow liquid having a viscosity of 460 cps and a Gardner color of 4. Equipment used was a 500 ml reaction flask, thermometer, Dean-Stark condenser and sparge tube.

EXAMPLE X

Mono-methoxy trans-1,4-cyclohexane dimethylol monomethacrylate (A) Preparation of mono-methoxy trans-1,4-cyclohexane dimethanol 448.7 grams trans-1,4-cyclohexane dimethanol (CHDM) were melted and charged to a prewarmed pressure reactor. Using the procedure of Example I part (B), mono-methoxy trans-1,4-cyclohexane dimethylol was prepared from the following:

| Material | Amount (gms.) |
|---|---|
| trans-1,4-cyclohexane dimethanol | 448.7 |
| sodium hydroxide | 124.8 (introduced in two portions) |
| methyl chloride | 157.4 (introduced in two portions) |

Product was a clear light yellow liquid having a hydroxyl number of 488. Color based on a Lumetron reading using No. 420 filter was 94.5 and viscosity was 308 cps at 25° C.

(B) Preparation of mono-methoxy trans-1,4-cyclohexane dimethylol mono-methacrylate Using the procedure and equipment of Example I part (C) mono-methoxy trans-1,4-cyclohexane dimethylol monomethacrylate was prepared from the following:

| Material | Amount (gms.) |
|---|---|
| mono-methoxy trans-1,4-cyclohexane dimethanol | 50.04 |
| toluene + inhibitors | 26.56 |
| p-toluene sulfonic acid | 1.37 |
| methacrylic acid | 39.33 |

The product was a whitish/yellow, semisolid product at room temperature. With slight heating the product was a clear yellow liquid, Gardner color 3.

EXAMPLE XI

Mono-methoxy, propoxylated hexylene glycol monomethacrylate having an average of two moles of propylene oxide (A) Preparation of hexylene glycol having an average of two moles of propylene oxide Using the procedure of Example I part (A), propoxylated hexylene glycol having an average of two moles of propylene oxide was prepared from the following:

| Material | Amount (gms.) |
|---|---|
| hexylene glycol | 395 |
| propylene oxide | 388 |
| BF₃ etherate | 1.1 |

The final product had a maximum Gardner color of 2 and a hydroxyl number of 335.

(B) Preparation of mono-methoxy propoxylated hexylene glycol having an average of two moles of propylene oxide Using the procedure of Example I (part B), mono-methoxy, propoxylated hexylene glycol having an average of two moles of propylene oxide was prepared from the following:

| Material | Amount (gms.) |
|---|---|
| hexylene glycol having an average of two moles of propylene oxide from part (A) | 489.2 |
| sodium hydroxide | 83.6 (introduced in two portions) |
| methyl chloride | 105.4 (introduced in -continued

| Material | Amount (gms.) |
|---|---|
| | two portions) |

The product was a clear, yellow liquid with a Brookfield viscosity of 15 cps (No. 1 spindle at 60 rpm at 25° C.). It had a hydroxyl number of 158.

(C) Preparation of mono-methoxy propoxylated hexylene glycol monomethacrylate, having an average of two moles of propylene oxide Using the procedure of Example I part (C), mono-methoxy propoxylated hexylene glycol monomethacrylate, having an average of two moles of propylene oxide was prepared from the following:

| Material | Amount (gms.) |
|---|---|
| mono-methoxy, propoxylated hexylene glycol having an average of two moles propylene oxide from part (B) | 127.10 |
| toluene + inhibitors | 61.80 |
| p-toluene sulfonic acid | 3.42 |
| methacrylic acid | 33.87 |

The product was a clear amber liquid with a Brookfield viscosity of 6 cps (No. 1 spindle at 60 rpm at 25° C.). The product had a Gardner color of 5.

EXAMPLE XII

Mono-methoxy, ethoxylated trimethylolpropane dimethacrylate having an average of three moles of ethylene oxide (A) Preparation of trimethylol propane having an average of three moles of ethylene oxide Using the procedure of Example I part (A), ethoxylated trimethylolpropane having an average of three moles ethylene oxide was prepared from the following:

| Material | Amount (gms.) |
|---|---|
| trimethylolpropane | 55.56 |
| ethylene oxide | 43.99 |
| sodium hydroxide | 0.50 |

The final product obtained had a maximum Gardner color of 2, a hydroxyl number of 689-700 and a viscosity of 850-950 cps (No. 2 spindle at 30 rpm at 25° C.).

(B) Preparation of mono-methoxy ethoxylated trimethylolpropane having an average of three moles of ethylene oxide Using the procedure of Example I, part (B), mono-methoxy ethoxylated trimethylolpropane having an average of three moles of ethylene oxide was prepared from the following:

| Material | Amount (gms.) |
|---|---|
| trimethylolpropane having an average of three moles ethylene oxide from part (A) | 690.4 |
| sodium hydroxide | 114 (introduced in two portions) |
| methyl chloride | 154 (introduced in two portions) |

The product was a clear, yellow liquid with a Brookfield viscosity of 180 cps (No. 2 spindle at 60 rpm at 25° C.) and had a hydroxyl number of 513.

(C) Preparation of mono-methoxy ethoxylated trimethylolpropane dimethacrylate, having an average of three moles of ethylene oxide Using the procedure of Example I, part (C), mono-methoxy ethoxylated trimethylolpropane dimethacrylate, having an average of three moles of ethylene oxide was prepared from the following:

| Material | Amount (gms.) |
|---|---|
| mono-methoxy, ethoxylated trimethylolpropane having an average of three moles of ethylene oxide from part (B) | 93.53 |
| toluene + inhibitors | 64.1 |
| p-toluene sulfonic acid | 5.15 |
| methacrylic acid | 77.79 |

The product was a clear yellow liquid with a Brookfield viscosity of 32.5 cps (No. 2 spindle at 60 rpm at 25° C.). The product had a Gardner color of 3.

EXAMPLE XIII

In this example, a number of lower alkyl ether alkoxylated and non-alkoxylated methacrylates were evaluated with a topical photoinitiator or catalyst. The cure rates are reported as cure speeds (feet/min.). Percent by weight of catalyst is percent by weight of total of catalyst plus monomer. The data is set forth in Table I.

Listed below are the abbreviations for the compounds appearing in the table. Where repeated, these abbreviations will have the same meaning.

| | |
|---|---|
| PEME(PO)4TMA | mono-methoxy propoxylated (4 moles) pentaerythritol trimethacrylate |
| TMPTMA | trimethylolpropane trimethacrylate |
| TMPME(EO)3DMA | mono-methoxy ethoxylated (3 moles) trimethylolpropane trimethacrylate |
| TMPME(PO)3DMA | mono-methoxy propoxylated (3 moles) trimethylolpropane trimethacrylate |
| TMP(EO)3TMA | trimethylolpropane ethoxylated (3 moles) trimethacrylate |
| GLYME(PO)3DMA | mono-methoxy, propoxylated (3 moles) glycerol dimethacrylate |
| CHDMEMMA | mono-methoxy trans-1,4-cyclohexane dimethylol monomethacrylate |
| HGME(PO)2MMA | mono-methoxy propoxylated (2 moles) hexylene glycol monomethacrylate |

Referring to Table I, the parent acrylates, i.e., those not containing an ether group consistently exhibited the slowest cure response. In some instances, the reactivity of the methyl ether alkoxylated acrylate analogs was not as quite as high as their precursors due to some unknown influence of the substrate. The monofunctional ether methacrylates generated relatively similar cure responses. This is most surprising as typical monofunctional methacrylates are slow curing, forming tacky coatings with little integrity and almost no crosslink character.

TABLE IX

Photoreactivity Evaluation
Cure Speed (feet/min.)

| Compound | Acrylate Functionality | 6% BP by wt. 2% TEOA by wt. |
| --- | --- | --- |
| TMPTMA | 3 | 0.3 |
| TMPME(PO)₃DMA | 2 | 2 |
| TMPME(EO)₃DMA | 2 | 2 |
| TMP(EO)₃TMA | 3 | 0.6 |
| GLYME(PO)₃DMA | 2 | 3 |
| PEME(PO)₄TMA | 3 | 2 |
| CHDMEMMA | 1 | 0.6 |
| HGME(PO)₂MMA | 1 | 0.4 |

Cure conditons:
One 300 watt/inch Fusion H lamp (mercury);
0.27 mil wet film aluminum substrate
BP = benzophenone
TEOA = triethanolamine In addition to reactivity, radiation curable diluents, as pointed out above, contribute to the final properties of the cured film. That is, they may modify or influence important properties of the oligomers in the cured coating such as hardness, flexibility, shrinkage, tensile strength and elongation. These properties are important parameters for coating materials since they influence the ultimate application of the coating materials. Table X below details these properties with respect to the methacrylate derived radiation hardenable diluents. Quantities of photocatalyst are percent by weight of monomer.

TABLE X

Selected Properties
Methacrylate Monomers with Benzophenone
(6%), TEOA (2%)
Aluminum Substrate

| Compound | Scuff Resist | Gloss 60° | MEK Rubs | Pencil Hard | % Adhes (X-Hatch) | % Shrink | Viscosity cps |
| --- | --- | --- | --- | --- | --- | --- | --- |
| TMPTMA | G | G | 100 | 3H | 0 | — | 55 |
| TMPME(PO)₃DMA | G | G | 100 | 3H | 0 | 11.5 | 62.5 |
| TMPME(EO)₃DMA | G | G | 45 | 4H | 0 | 7.8 | 32.5 |
| TMP(EO)₃TMA | G | G | — | 4H | 0 | — | 45.0 |
| GYLME(PO)₃DMA | G | G | 20 | 2H | 0 | 18.6 | 67.5 |
| PEME(PO)₄TMA | G | G | 37 | H | 0 | 5.8 | 460 |
| CHDMEMMA | G | G | 100 | 5H | 40 | 8.2 | Solid |
| HGME(PO)₂MMA | F | G | 7 | 4B | 100 | 11.3 | 15 |

Referring to the data of Table X for the photocatalysts studied, there were no dramatic differences in gloss, MEK or scuff resistance of the homopolymers made from the methoxy methacrylates over the parent monomers.

In the derivative series tested, the pencil hardness was unchanged or slightly higher in ratings. Overall, UV cured films of methoxy methacrylates generated film hardness ratings equal to the parent methacrylates. A possible explanation is that because it takes so long to cure, the higher values may be due to thermal rather than UV cure.

Regarding adhesion to aluminum, a few of the methoxy methacrylates exhibited varying degrees of adhesion ranging from 40-100% based on cross-hatch studies with Cellotape #600. Past experience has shown that good to excellent adhesion of reactive monomers to metals and plastics is very difficult to achieve because of surface energy differences, substrate hydrophobicity, high shrinkage on cure and high crosslink density. The reactive monomers that developed good to excellent adhesion were CHDMEMMA and HGME(PO)₃MMA, both monofunctional methoxy methacrylates.

As indicated previously, a reactive monomer property that is particularly important in developing good adhesion is film shrinkage of the homopolymer on curing. The methacrylate results were similar to the acrylates where the methyl ether derivatives gave lower shrinkage values than the parent compounds.

Further, with the methacrylate derived monomers, another measure of the utility of the reactive diluents is their solvating efficiency or reducing power. Although they may exhibit similar neat viscosities, they do not necessarily produce identical solution viscosities in the presence of an equal amount of oligomer.

A number of factors affect the final solution viscosity including the solvating efficiency and neat viscosity of the monomer. Table XI below details the solution viscosities obtained with selected methacrylate derived monomers in the presence of a high viscosity epoxy acrylate oligomer, i.e., bis-phenol A diglycidylether diacrylate having a neat viscosity of 2,000,000 cps at 25° C.

TABLE XI

Viscosity Reduction Comparison
Selected Methacrylates vs. Methoxy Methcrylate Derivatives
in Epoxy Acrylate Oligomer*

| Compound | Monomer Viscosity (cps) | Solution Viscosity (cps) |
| --- | --- | --- |
| TMPTMA | 55 | 2700 |
| TMPME(PO)₃DMA | 62.5 | 5600** |
| TMPME(EO)₃DMA | 32.5 | 850 |
| TMP(EO)₃TMA | 123.8 | 3900** |
| GYLME(PO)₃DMA | 67.5 | 1550 |
| PEME(PO)₄TMA | 460 | 2600 |
| CHDMEMMA | Solid | 600 |
| HGME(PO)₂MMA | 15 | 400 |

*Conditions: 47% by wt. Oligomer, 47% by wt. Monomer, 6% by wt. Benzophenone
Brookfield, #4 spindle, at 60 RPM, 25° C.
**Higher solution viscisities reflect presence of undesired methacrylate homopolymer resulting in a higher than expected solution viscosity.

For the reactive diluents tested, the methoxy ether methacrylates were more effective than the parent from which they were derived. When compared against TMPTMA, their viscosity reducing characteristics ranged from 50-90% more efficient with high viscosity epoxy acrylate oligomers.

To test the efficacy of the lower alkoxy methacrylates, the monomers were evaluated in a formula which is typical of radiation curable systems. In the simplest case, this is comprised of a reactive oligomer, reactive monomer (diluent) and photocatalyst. Table XII details the products tested and the experimental conditions employed.

TABLE XII

Radiation Curable System
Methacrylates vs. Methoxy Derivatives
(Wt. %)

| | Formulations | | | | | | |
|---|---|---|---|---|---|---|---|
| | 1 | 2 | 3 | 4 | 5 | 6 | 7 |
| Compound | | | | | | | |
| BPA Diglycidylether* diacrylate oligomer | 47 | 47 | 47 | 47 | 47 | 47 | 47 |
| TMPTMA | 47 | | | | | | |
| TMPME(PO)$_3$DMA | | 47 | | | | | |
| TMPME(EO)$_3$DMA | | | 47 | | | | |
| GLYME(PO)$_3$DMA | | | | 47 | | | |
| PEME(PO)$_4$TMA | | | | | 47 | | |
| CHDMEMMA | | | | | | 47 | |
| HGME(PO)$_2$MMA | | | | | | | 47 |
| Benzophenone | 6 | 6 | 6 | 6 | 6 | 6 | 6 |
| Properties | | | | | | | |
| Cure Speed (Ft/Min) | 1 | 13 | 5 | 8 | 6 | 4 | 4 |
| Scuff | G | G | G | G | G | G | G |
| Gloss | G | G | G | G | G | G | G |
| Pencil Hardness | 3H | 3H | 2H | 2H | 4H | 3H | 4H |
| MEK Rubs | 100 | 100 | 40 | 70 | 100 | 55 | 8 |
| Conical Mandrel (inches) | <0.25 | <0.25 | <0.25 | <0.25 | <0.25 | <0.25 | <0.25 |

Conditions: Aluminum panels (Q-Panel Corp); One 300 watt inch Mercury Lamp; 0.27 Wet Mil Film; RDS #3 Rod; 25 ft/min.
BPA Diglycidylether = Bisphenol A diglycidylether diacrylate having a neat viscosity of 2,000,000 cps at 25° C.

The properties generated from the coating compositions of Table XII unequivocally support the results generated from the comparable studies conducted on the neat monomers. In the TMP family, reactivity of the system incorporating the methoxy analog was equal to or greater than the parent from which it was derived. There was no loss in scuff or gloss in the methoxy methacrylate formulations. Pencil hardness ratings and the MEK rubs also mirrored the results previously described for the neat monomers.

Further, in this radiation curable system, it was unexpected to find that the propoxylated methyl ether derivatives generated faster cures than both the corresponding ethoxylates and the unmodified methacrylates.

On balance, the lower alkoxy methacrylates in radiation curable mixtures enhance their reactivity compared to standard multifunctional methacrylates (e.g. TMPTMA), produce tack-free coatings of equivalent durability and solvent resistance.

As can be seen from the data presented, the lower alkyl ether methacrylates exhibit excellent cure response, low viscosity and outstanding solvency. They cure or harden under ultra-violet radiation to tack free homopolymers that exhibit significantly lower shrinkage than other methacrylate type monomers. Further, the radiation curable compositions which contain these lower alkyl ether methacrylates are also characterized by the enhanced properties shown by the neat monomers.

While the invention has been described with reference to certain specific embodiments thereof it is understood that it is not to be so limited since alterations and changes may be made therein which are within the full intended scope of the appended claims.

What is claimed is:

1. A lower alkyl ether which is mono-methoxy ethoxylated 2,2-bis(p-hydroxyphenyl) propane having an average of about four moles of ethylene oxide.

* * * * *

UNITED STATES PATENT AND TRADEMARK OFFICE
CERTIFICATE OF CORRECTION

PATENT NO. : 5,243,085
DATED : September 7, 1993
INVENTOR(S) : Higbie et al.

It is certified that error appears in the above-indentified patent and that said Letters Patent is hereby corrected as shown below:

On title page, item [19] "hibie et al." should read --Higbie et al--
On the title page, at [75],"Hibie" should read -- Higbie --.

Signed and Sealed this

Twelfth Day of April, 1994

Attest:

BRUCE LEHMAN

Attesting Officer     Commissioner of Patents and Trademarks